(12) United States Patent
Kaoukab Raji

(10) Patent No.: US 6,194,724 B1
(45) Date of Patent: *Feb. 27, 2001

(54) SIMULTANEOUS ACQUISITION OF TRANSMITTED COUNTS AND EMITTED COUNTS FOR A GAMMA CAMERA

(75) Inventor: Anas Kaoukab Raji, Trappes (FR)

(73) Assignee: SMV International, Buc Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,134

(22) Filed: Sep. 5, 1997

(30) Foreign Application Priority Data

Sep. 5, 1996 (FR) .................................. 96 10999

(51) Int. Cl.[7] ...................................... G01T 1/166
(52) U.S. Cl. ..................... 250/363.04; 250/369
(58) Field of Search ..................... 250/363.03, 363.04, 250/363.02, 363.07, 369, 370.08, 370.09

(56) References Cited

U.S. PATENT DOCUMENTS 3,011,057  11/1961  Anger .
5,296,708  3/1994  Moyers et al. .................. 250/363.03
5,600,145 * 2/1997  Plummer .......................... 250/363.04
5,608,221 * 3/1997  Bertelsen et al. ............... 250/363.03

FOREIGN PATENT DOCUMENTS 470909  2/1992  (EP) .
526970  2/1993  (EP) .
WO 94/09383  4/1994  (WO) .

\* cited by examiner

Primary Examiner—Constantine Hannaher
Assistant Examiner—Albert Gagliardi
(74) Attorney, Agent, or Firm—Nilles & Nilles SC

(57) ABSTRACT

A simultaneous acquisition process of a transmission image and an emission image with a gamma camera equipped with a detector (3), the detector (3) being opposite the patient (5) who has received an injection of a first radioactive isotope emitting gamma-ray photons ($\gamma 2$) in a first energy range (P1), the process including the movement of a radioactive source (4) behind the patient (5), the source (4) consisting of a second isotope emitting gamma-ray photons ($\gamma 1$) in a second energy range (P2), and the production, during the detection of an impact of a gamma-ray photon on the detector (3) of the coordinates of the impact of the photon on the detector and information relevant to the energy of the photon during the impact, the process having the particularity that it differentiates between the photon impacts according to their energy levels and the position of the impact in relation to the position of the source (4).

10 Claims, 2 Drawing Sheets

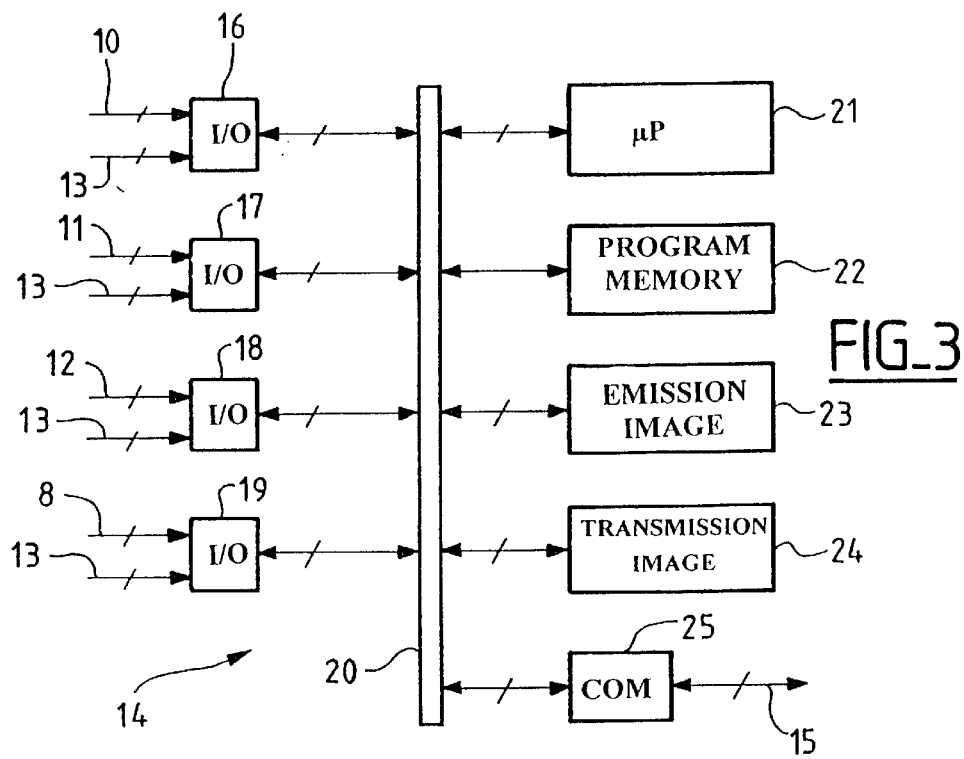
FIG_3
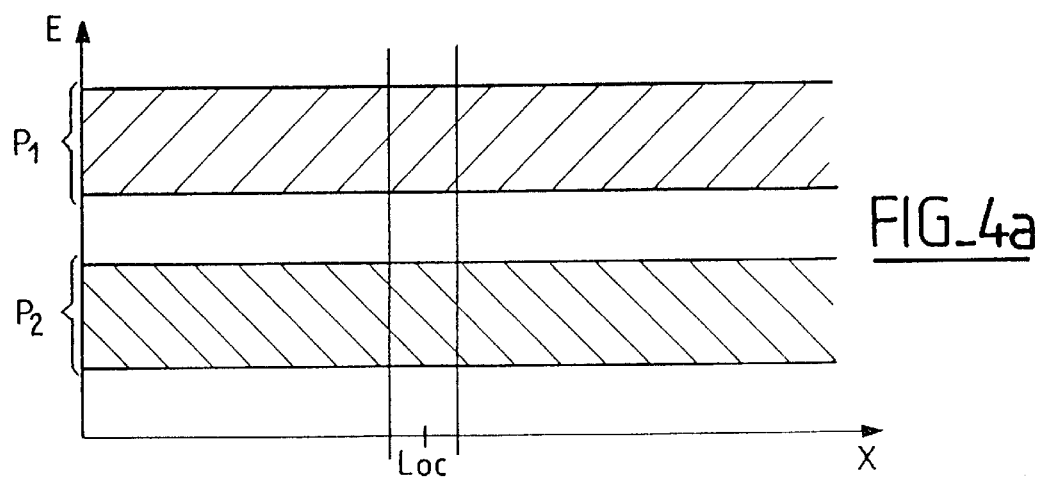
FIG_4a
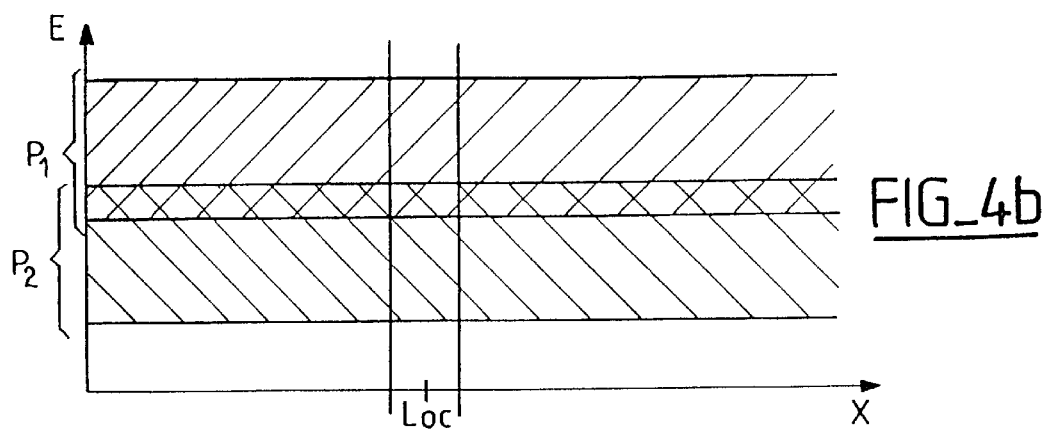
FIG_4b

SIMULTANEOUS ACQUISITION OF TRANSMITTED COUNTS AND EMITTED COUNTS FOR A GAMMA CAMERA

BACKGROUND OF THE INVENTION

The invention concerns simultaneous acquisition of transmitted counts and emitted counts for a gamma camera. It concerns, among others, scintillation cameras of the ANGER type for which document U.S. Pat. No. 3,011,057 describes its operating principles and its means of achievement.

In nuclear imaging systems, an image can be obtained in two different ways. A first method consists in placing a radioactive source opposite a detector and in placing the body or the object to be examined between the source and the detector. The result obtained using this first method is commonly called the "transmission image" by a person skilled in the art. This name comes from the fact that the radiations are transmitted through the body or the object. A second method consists in placing a detector opposite the object or the body to be examined. For a human body, one will have previously injected a radioactive isotope into the patient before the examination. The image obtained with this second method is commonly called the "emission image" as, with this method, the image is formed from the radiations emitted by the body under examination.

In nuclear medicine, the two types of images fulfil two different functions. The transmission image gives an image of the inside of the body which depends on the transparency of the various organs in relation to the radiation. The emission images however are used to display certain organs that it would be impossible to observe by transmission or to determine the operation of an organ in relation to the distribution of the radioactive isotope.

In an emission image, the distribution of the isotope depends on the fixation of the said isotope in the various organs, and the fixation depends on the type of isotope used and the various characteristics of each organ. Therefore, radiations are potentially emitted from all points of the human body. A part of these radiations must therefore pass through a part of the body. The emission image is altered by the scatter of gamma-ray photons passing through certain parts of the body under examination, causing a blurred image.

A solution to this problem consists in correcting the emission image by means of a transmission image. However, to be used to correct the emission image, the transmission image must be obtained under the same conditions as the emission image.

Gamma cameras can validate a gamma-ray photon impact (commonly called count) which occurs on their detectors as a function of the energy level of the said count received. A method consists in taking images simultaneously by separating the counts received as a function of the energy levels. A first radioactive isotope producing counts at a first energy level (for example 140 keV technetium) is injected into the patient, and a homogeneous source containing a second radioactive isotope producing counts at a second energy level (for example 100 keV gadolinium) is placed behind the patient. When the gamma camera detector receives a count, it is possible to detect whether it is a transmission or an emission according to the energy received.

Such a method has imperfections. The counts produced by the isotopes have a certain energy scatter requiring a certain width for the energy window to determine to which energy category the count belongs; in general, this window is designed with tolerances of 10 to 20% on the nominal energy which can vary as a function of the isotope in order to avoid an overlong exposure time for the patient. In addition, certain counts are converted into Compton diffusion with lower energy, the counts counted in the lower energy level recording are the Compton photons corresponding to the higher energy level counts. Concerning the accuracy of the transmission image, it is preferable to use isotopes as close as possible for the emitted count energy levels as the transmission phenomenon depends, among other things, on the energy of the photons.

To sum up, taking two images simultaneously tends to degrade the quality of both of the images. Solutions have been found to attempt to reduce the undesirable effects. It is possible to take images successively but this increases the duration of the examination and the risk of the patient moving. It is also possible to use a collimated source with a surface area lower than the size of the detector that is moved behind the patient in order to obtain a less degraded emission image.

OBJECTS AND SUMMARY OF THE INVENTION

The purpose of the invention is to reduce the interference problems between the two images mentioned above and to allow the use of radioactive isotopes whose emitted count energy levels are closer still. For this, the transmission image is taken by means of a translation movement window which is perfectly synchronised with a sliding arm carrying a source containing the transmission radioactive isotope.

Thus, the aim of the invention is a simultaneous transmission image and emission image acquisition process with a gamma camera equipped with a detector, the detector being placed opposite the patient who has received an injection of a first radioactive isotope emitting gamma-ray photons in a first energy range, the said process including the following steps:

movement of a radioactive source behind the patient, the said source consisting of a second isotope emitting gamma-ray photons in a second energy range, production, on the detection of an impact of a gamma-ray photon on the detector, of the coordinates of the impact of the photon on the detector and information relevant to the energy of the photon during the impact, characterised in that:

we compare the coordinates to a position of the source during the impact to determine whether they belong to an area of the detector opposite the source, and we consider that the impact belongs to a transmission image if the energy of the photon during the impact belongs to the second energy range and if the coordinates belong to the area of the detector opposite the source.

The use of a movable window thus limits the transmission and emission image exposure times in relation to the photons which could disturb each of the images. The influence of the emission gamma-ray photons on the transmission image is therefore reduced. In addition, we obtain a pure emission image to correct the pollution of the transmission image. Then, with two pure images, it is possible to correct the emission image using the transmission image.

The influence of the photons of the source on the emission image is compensated for by the fact that the source moves making exposure to the troublesome photons shorter. It is still possible to reduce the influence of the transmission gamma-ray photons on the emission image by considering that the impact belongs to an emission image if the energy of the photon during the impact belongs to the first energy range and if the coordinates do not belong to the area of the detector opposite the source.

Nevertheless, if we prefer to favour acquisition speed, we consider that the impact belongs to an emission image if the energy of the photon during the impact belongs to the first energy range.

Preferentially, we use a first energy range with an average energy higher than the average energy of the second energy range. Indeed, if the emission image corresponds to an energy higher than the transmission image, then the pollution of the emission image will be practically zero. We can also use energy ranges with a non-null intersection.

BRIEF DESCRIPTION OF THE DRAWINGS

The invention will be easier to understand and other characteristics will appear in the description which will follow, read in conjunction with the appended drawings on which:

FIGS. 2 and 3 functionally represent a gamma camera according to the invention,

FIGS. 4a and 4b show different usable energy ranges.

DESCRIPTION OF THE PREFERRED EMBODIMENTS

Figure 1:
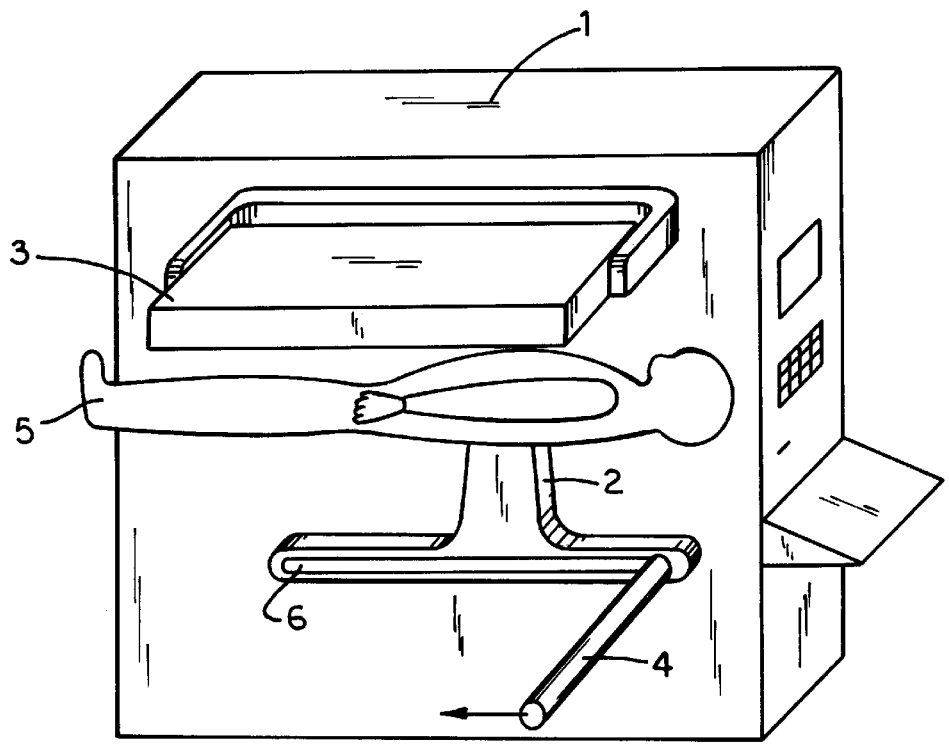
FIG. 1 shows a gamma camera according to the invention with a patient.

On FIG. 1, we can see a gamma camera 1 which includes an articulated arm 2. The articulated arm 2 supports, on the one hand, a detector 3 and, on the other hand, a movable source 4. A patient 5 being examined is placed between the movable source 4 and the detector 3, the patient having previously received a first radioactive isotope (for emitting gamma-ray photon γ1); by injection. To support the patient 5, a patient-carrier bed is conventionally used; it has not been shown in order to keep the drawing simple.

Conventionally, the articulated arm 2 is used to place one or more detectors 3 in different positions in space. The articulated arm includes a rail 6 to allow a movable source 4 to move. The movable source 4 can consist of a tube, transparent to gamma radiations, which contains a second isotope different from the first isotope (i.e., for emitting gamma-ray photons γ2).

In our example, the movable source 4 is a tube slightly longer than the width of the detector 3 and with a small diameter but it could just as well have any geometrical shape. Certain conditions are to be complied with on the movable source 4. The projection surface area of the movable source 4 on the detector 3 must be lower than the effective surface area of this detector 3. Also, the geometrical shape of the movable source 4 must allow homogeneous scanning of the surface of the detector 3. The scanning can be achieved on a part of the total surface if the image to be corrected corresponds to a region of interest smaller than the total contact surface area 30 of the detector in order to reduce the quantity of isotope to be used. The movable source 4 can also make translation movements along several axes if its shape requires this. Note that the smaller the volume of the movable source 4, the smaller the quantity of radioactive product contained in the movable source 4 thus reducing the risk of exterior contamination and the costs. The choice of a tube enables simple use both for the mechanical parts and for the processing electronics. Indeed, mechanically, only a single translation movement is to be made and, electrically, we simply have an imaging strip which moves along only one of the coordinates.

Figure 2:
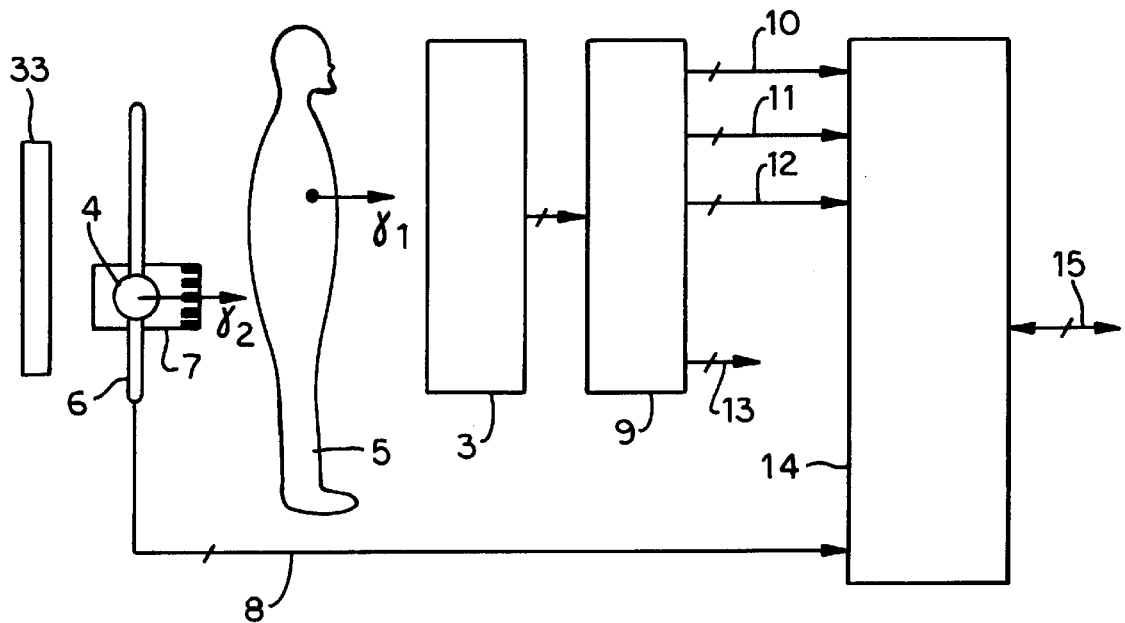

FIG. 2 shows a side view of the detector 3, the movable source 4 and the patient 5. Also, this FIG. 2 shows the functional elements of the gamma camera comprising the image acquisition electronics (described below) which cannot be seen on FIG. 1.

Functionally, the detector 3 consists of a collimator which only lets through photons arriving perpendicular to the detector 3, a scintillator which converts the energy of the gamma-ray photon which has passed through the collimator into light energy, photomultiplier tubes which convert the light energy given off by the scintillator into electric signals and a set of arrays which weight the electric signals in order to deliver a weighted signal bus. For further details on such a detector 3, it is possible to refer, for instance, to document EP-A-0 470 909. Also, other types of semiconductor detectors delivering unweighted digital signals can be used without calling the invention into question, only the previously described impact detection circuits need to be adapted to suit.

In order to reduce the quantity of radiations received by the patient, a collimator 7 is placed over the source. This collimator is not indispensable, but it limits the radiations produced by the source to the radiations useful for the transmission image, thus eliminating the unwanted radiation harmful to the patient. Such a collimator 7 consists of a material opaque to the radiations of the source 4 and completely covers the source 4. Small diameter holes 32 (diameter lower than the length of the holes) let gamma-ray photons γ2 through only if they are perpendicular to the detector 3. We therefore consider that the source 4 is collimated.

The rail 6 provides information on the position of the source 4 on a location bus 8. This information can be produced either by a sensor system 33 which detects the position of the source 4 or by a system which positions the source and controls the position of the source independently. The location bus 8 can consist, for instance, of eight wires, which give sufficient accuracy to identify the position of the source.

A calculation circuit 9 receives the weighted signal bus from the detector 3 to calculate the position of the impact of a gamma-ray photon received and the energy of the gamma-ray photon received. The calculation circuit 9 delivers information relevant to the X-axis position on a first position bus 10, information relevant to the Y-axis position on a second position bus 11, information relevant to the energy on an energy bus 12, and information of impact received on a control bus 13. The control bus 13 is a bus global to the entire acquisition system and is used to manage the synchronisation of the various elements which need to be synchronised in relation to each other. Such a calculation circuit 9 is shown, for instance, in document EP-A-0 470 909 and can be quite easily replaced by one of the many equivalent circuits. For reasons of simplicity and performance, we preferably use a digital calculation circuit 9 but an analogue circuit can just as well be used. The two position buses 10 and 11 and the energy bus 12 consist for instance of eight wires each in order to obtain minimum accuracy required.

An acquisition circuit 14 receives the location bus 8, the two position buses and 11, and the energy bus 12. This acquisition circuit 14 also has a communication bus 15 for exchanging data with, for instance, an image correction system which modifies an emission image according to a transmission image. The said acquisition circuit 14 allows the impacts of the gamma-ray photons received to be differentiated according to the energy level of the photons and position of the impact in relation to the position of the source 4. The acquisition circuit 14 can consist, for instance, of a microprocessor circuit such as the one on FIG. 3. If the various buses 10, 11, 12 and 8 are replaced by analogue-type signals, microcontrollers with analogue inputs can be used.

FIG. 3 shows four input/output interfaces 16 to 19 each receiving an input bus which is one of the buses from among the location bus 8, the position buses 10 and 11, and the energy bus 12. Each of the interfaces 16 to 19 also receives synchronisation signals from the control bus 13. Each of the interfaces 16 and 19 also has a processing input/output which is connected to a central bus 20. The interfaces 16 to 19 are identical and each one has a FIFO (First-In/First-Out) type buffer memory. When the synchronisation signals of the control bus 13 indicate that an impact has been detected and that the bus connected to the interface supports valid information, then the information present on the input bus are stored in the buffer memory.

The central bus 20 corresponds to the grouping of the various buses of a microprocessor 21. In addition, the acquisition circuit 14 also includes a program memory 22, an emission image memory 23, a transmission image memory 24, and a communication port 25. The three memories, 22 to 24, are connected to the central bus 20; these three memories, 22 to 24, may physically be one and the same memory. The communication port 25 is connected, on the one hand, to the central bus 20 and, on the other hand, to the communication bus 15. Conventionally, it is possible to use an RS232-type serial interface as communication port 25.

A person skilled in the art will have immediately understood that FIG. 3 corresponds to a microcomputer- or microcontroller-type architecture. For an architecture of this type, the complete operation depends on the program which is placed in the program memory 22.

From the process given in the preamble, several programs and algorithms can be defined. Preferably, the following algorithm is produced:

read from interfaces 16 to 19, if the buffer memories are empty, then wait a certain time and restart this step, else continue execution of the algorithm, comparison of the level of the energy of the photon during impact with the minimum and maximum thresholds of the energy ranges corresponding to the first and second radioactive isotopes, production of a difference variable giving the difference in absolute value between the X-axis of the coordinates of the impact of the photon on the detector 3 and the location information of the source 4, setting of a Boolean variable to 1 if the difference variable is lower than or equal to the half-width of the tube comprising the source 4, and setting of this Boolean variable to 0 if the difference variable is greater than a half-length of the tube comprising the source 4, if the energy of the photon belongs to the energy range which corresponds to the first isotope and if the Boolean variable is set to 0 then the impact will be acquired for the emission image, if the energy of the photon belongs to the energy range which corresponds to the second isotope and if the Boolean variable is set to 1 then the impact will be acquired for the transmission image, the algorithm is repeated from the beginning whilst image acquisition is not complete.

Of course, during the execution of the algorithm, the source 4 behind the patient is moved independently.

In a variant, we can also acquire two other images, one corresponding to the emission image taken inside the transmission window and the other corresponding to a transmission image taken outside of the transmission window. These images can be used to correct the transmission image taken in the transmission window which is "polluted" by the emission isotope and to make an additional correction directly on the emission image taken outside of the transmission window. In fact, only one of these images is useful and it depends on the choice of isotope.

The Boolean variable of the algorithm reflects the comparison of the coordinates with a position of the source 4 during the impact in order to obtain binary data indicating whether they belong to an area of the detector 3 opposite the source 4. In our example, the comparison with the X-axis is sufficient as we have chosen a tube with a length which covers the complete width of the detector 3. Therefore, the comparison of the coordinates is made only with one of the coordinates, and the area of the detector 3 opposite the source 4 corresponds to a strip of the detector 3 over the complete width and which moves over the complete length. Of course, the Y-axis can replace the X-axis according to the position of the tube in relation to the detector 3. In addition, if the source 4 has another shape (rectangle or circle of size lower than the detector 3, or other) the two coordinates would have to be taken into account to determine whether they belong to an area of the detector 3 opposite the source 4. As stated previously, scanning may concern only a part of the surface area of the detector.

It is possible to use a mask memory, commonly called bitmap, to check whether the coordinates of the impact belong to the area of the detector 3 opposite the source 4. A mask corresponding to the shape of the source is displaced in the mask memory according to the location information (this being especially attractive when the source is not a tube). The mask memory consists of bits either at 0 or at 1 depending on whether they belong to the image or not. When an impact occurs, one need simply consult the mask memory by means of the impact coordinates; the state of the bit read (0 or 1) tells us whether it belongs to the area of the detector 3 opposite the source 4.

With the algorithm, the impact is considered as belonging to an emission image if the energy of the photon during the impact belongs to the first energy range and if the coordinates do not belong to the area of the detector 3 opposite the source 4, or the impact is considered as belonging to a transmission image if the energy of the photon during the impact belongs to the second energy range and if the coordinates belong to the area of the detector 3 opposite the source 4.

If we refer to FIGS. 4a and 4b, the diagrams show the impact point of the photon on the detector 3 on the X-axis and the energy of the photon during the impact on the Y-axis. On each of the drawings, we have represented, on the X-axis, the location information Loc from which, on each side, at a distance corresponding to the width of the tube, we have drawn vertical lines defining the area of the detector 3 opposite the source 4. The energy ranges P1 and P2 which correspond respectively to the first energy range and the second energy range in our example are placed on the Y-axis (they can of course be inverted). These energy ranges, P1 and P2, are separate on FIG. 4a and overlap on FIG. 4b.

On FIG. 4a, one may think that, as the two energy ranges are separate, a differentiation based only on the energy, as in the previous state of the art, would be sufficient.

However, if we take, for instance, a technetium isotope as the first isotope and a gadolinium isotope as the second isotope, the energy ranges, P1 and P2, would be centred on 140 keV and 100 keV respectively with ranges at ±10%, we are in the case of FIG. 4a but the problem is as follows: a certain number of gamma-ray photons exist which are converted into Compton diffusion with an energy level around 30 keV lower, the Compton photons obtained from the photons originally of an energy level which is included in the energy range of the higher energy level are found in the energy range of the lower energy level.

The use of the invention eliminates the effects of the pollution of the emission image by the photons intended for the transmission image and greatly reduces the effects of the pollution of the transmission image by the emission image by a ratio with an order of magnitude equal to the ratio of the surface areas of the detector 3 and the area of the detector 3 opposite the source 4. This allows us to consider higher energy ranges or to use isotopes with closer energy levels (hence an improvement in image correction), the energy ranges having a non-null intersection.

Nevertheless, the process as described slightly slows down the acquisition of the emission image. This is due to the fact that we do not take into account the impacts in the first range when their coordinates correspond to the area of the detector 3 opposite the source 4. However, under certain conditions, such as spaced out ranges and/or a first energy range which has an average energy level higher than the average energy level of the second energy range, the disturbances to the emission image are negligible and there is therefore no need to correct them. However, the disturbances affecting the transmission image are still present and high and must still be corrected. We therefore add to the algorithm a step where we consider that the impact on the detector 3 belongs to an emission image if the energy of the photon during the impact belongs to the first energy range and if the coordinates belong to the area of the detector 3 opposite the source 4.

Or again, which comes down to the same, it is possible to replace the step:
if the energy of the photon belongs to the energy range which corresponds to the first isotope and if the Boolean variable is set to 0 then the impact will be acquired for the emission image, by the step:
it the energy of the photon belongs to the energy range which corresponds to the first isotope the impact will be acquired for the emission image,
which no longer takes into account the position of the source 4 if the energy of the gamma-ray photon belongs to the first energy range.

As a person skilled in the art may have understood, we will prefer that the average energy of the first energy range be greater than the average energy of the second energy range.

Many modifications can be made whilst remaining within the spirit of the invention. Thus, different processes for detecting and processing the impacts of the photon on the detector can be used. Also, different processes can be used for acquiring an image from the coordinates of the impact of a photon when the impact is declared valid. In addition, all available isotopes can be used.

What is claimed is:

1. A process for simultaneous acquisition of a transmission image and an emission image with a gamma camera equipped with a detector, the detector having a total surface area and being arranged opposite a patient who has received an injection of a first radioactive isotope emitting gamma-ray photons (γ1) in a first energy range (P1), the process comprising the steps of:
   moving a radioactive source adjacent to the patient and in a first direction generally parallel to the longitudinal axis of the patient, said source consisting of a second isotope emitting gamma-ray photons (γ2) in a second energy range (P2), and wherein said source has a projection surface area smaller than the total surface area, and is configured and arranged to provide homogeneous scanning of the total surface area of the detector;
   detecting an impact of a photon on the detector;
   determining (1) coordinates of the impact of the photon on the detector and (2) an energy of the photon during the impact;
   comparing the coordinates to a position (Loc) of said source during the impact to determine whether the coordinates correspond to an area of the detector opposite said source;
   considering that the impact belongs to a transmission image if (1) the energy of the photon corresponds to said second energy range (P2) and (2) the coordinates correspond to the area of the detector opposite said source;
   repeating each of the above steps to collect data to simultaneously create the transmission image and the emission image; and
   wherein the first and second energy ranges (P1 and P2) have a non-null intersection.

2. The process in accordance with claim 1, wherein the impact is considered as belonging to an emission image if the energy of the photon during the impact corresponds to the first energy range (P1) and if the coordinates do not correspond to the area of the detector opposite said source.

3. The process in accordance with claim 1, wherein said comparing step is made with only one of the coordinates, and wherein the area corresponds to a strip of the detector.

4. The process in accordance with claim 1, wherein said predetermined condition is characterized by an average energy of the first energy range (P1) that is higher than an average energy of the second energy range (P2).

5. The process in accordance with claim 1, wherein the source is collimated.

6. The process in accordance with claim 1, wherein said source extends transversely to the longitudinal axis of the patient.

7. The process in accordance with claim 1, wherein said moving step further includes moving said source in a second direction, said first direction and said second direction collectively defining a generally horizontal plane generally parallel to the patient.

8. The process in accordance with claim 1, further including the step of modifying the emission image based on the transmission image.

9. The process in accordance with claim 1, further comprising the step of using a sensor system to detect the position of said source.

10. A process for simultaneous acquisition of a transmission image and an emission image with a gamma camera equipped with a detector, the detector having a total surface area and being arranged opposite a patient who has received an injection of a first radioactive isotope emitting gamma-ray photons (γ1) in a first energy range (P1), the process comprising the steps of:
   moving a radioactive source adjacent to the patient, said source consisting of a second isotope emitting gamma-ray photons (γ2) in a second energy range (P2);

detecting an impact of a photon on the detector;

determining an energy of the photon during the impact;

identifying a location of the impact of the photon on the detector;

comparing the location to a position (Loc) of said source during the impact to determine whether the location corresponds to an area of the detector opposite said source;

considering that the impact belongs to a transmission image if (1) the energy of the photon corresponds to said second energy range (P2) and (2) the location corresponds to the area of the detector opposite said source;

repeating each of the above steps to collect data to simultaneously create the transmission image and the emission image; and wherein the first and second energy ranges (P1 and P2) have a non-null intersection.

* * * * *